(12) United States Patent
Wilson et al.

(10) Patent No.: US 9,796,997 B2
(45) Date of Patent: *Oct. 24, 2017

(54) DETECTION OF BACTERIA AND FUNGI

(71) Applicant: MOMENTUM BIOSCIENCE LTD, London (GB)

(72) Inventors: Stuart Wilson, London (GB); William Mullen, Reading (GB)

(73) Assignee: Momentum Bioscience Limited, Cardiff (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/805,583

(22) Filed: Jul. 22, 2015

(65) Prior Publication Data

US 2015/0322478 A1 Nov. 12, 2015

Related U.S. Application Data

(63) Continuation of application No. 13/264,177, filed as application No. PCT/GB2010/000781 on Apr. 19, 2010, now Pat. No. 9,096,884.

(30) Foreign Application Priority Data

Apr. 17, 2009 (GB) .................................. 0906643.2
May 7, 2009 (GB) .................................. 0907785.0

(51) Int. Cl.
*C12Q 1/04* (2006.01)
*C12Q 1/68* (2006.01)

(52) U.S. Cl.
CPC ............... *C12Q 1/04* (2013.01); *C12Q 1/689* (2013.01); *C12Q 1/6895* (2013.01); *C12Q 1/68* (2013.01); *C12Q 2521/501* (2013.01); *C12Q 2527/119* (2013.01); *C12Q 2533/10* (2013.01); *C12Q 2537/149* (2013.01); *G01N 2333/9015* (2013.01)

(58) Field of Classification Search
None
See application file for complete search history.

(56) References Cited

U.S. PATENT DOCUMENTS

| 9,096,884 B2 | 8/2015 | Wilson et al. |
| 2006/0024723 A1 | 2/2006 | Hussa et al. |
| 2006/0281899 A1 | 12/2006 | Kulomaa et al. |
| 2010/0184046 A1 | 7/2010 | Klass et al. |

FOREIGN PATENT DOCUMENTS

| EP | 0 373 962 | 6/1990 |
| EP | 1 693 672 | 8/2006 |
| WO | WO 02/46453 | 6/2002 |
| WO | WO 03/102590 | 12/2003 |
| WO | WO 2005/093089 | 10/2005 |
| WO | WO 2009/007719 | 1/2009 |

OTHER PUBLICATIONS

Heppel et al. J. Supramolec. Strucutre (1977) 6: 399-409.*
Dwivedi, et al. (2008) Medicinal Research Reviews 28(4): 545-568.
Haltiwanger, et al. (2000) Biochemistry 39: 763-772.
Wilkinson, et al. (2001) Molecular Microbiology 40(6): 1241-1248.
International Search Report for International Application No. PCT/GB2010/000781, mailed Jun. 28, 2010.
Written Opinion for International Application No. PCT/GB2010/000781, mailed Jun. 28, 2010.

* cited by examiner

*Primary Examiner* — Susan Hanley
(74) *Attorney, Agent, or Firm* — Hunton & Williams LLP

(57) ABSTRACT

A method of detecting a ligase expressing micro-organism in a sample comprises steps of treating the sample under conditions that inhibit the activity of ATP-dependent ligase from mammalian cells but which do not inhibit the activity of the microbial ligases, contacting the sample or a portion of the sample with a nucleic acid molecule which acts as a substrate for ligase activity in the sample, incubating the thus contacted sample under conditions suitable for ligase activity; and specifically determining the presence and/or the amount of a ligated nucleic acid molecule resulting from the action of the ligase on the substrate nucleic acid molecule to indicate the presence of the ligase expressing micro-organism. The micro-organism may be a fungus or a bacterium or both. High pH conditions may be employed to inactivate mammalian ligases. Related kits are described.

19 Claims, 1 Drawing Sheet

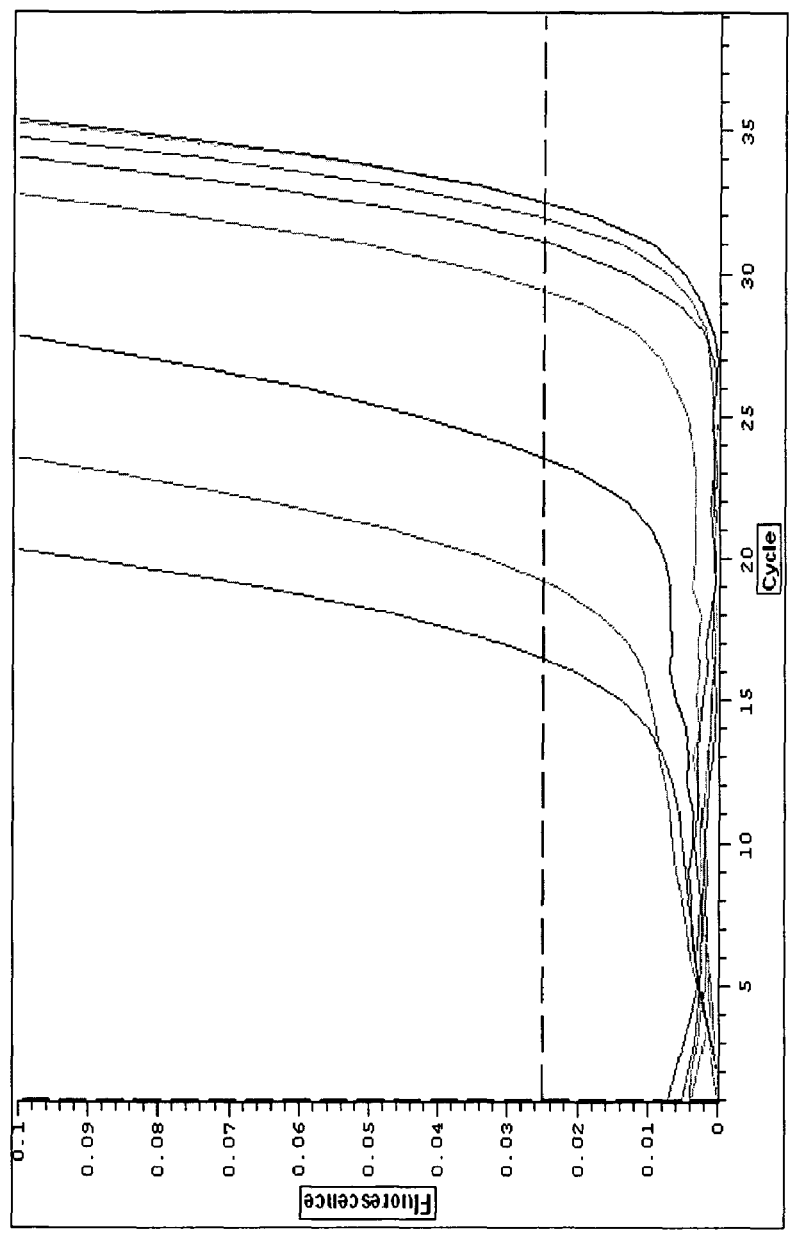

DETECTION OF BACTERIA AND FUNGI

CROSS REFERENCE TO RELATED APPLICATION

The subject application is a continuation patent application of U.S. application Ser. No. 13/264,177, now U.S. Pat. No. 9,096,884, filed Jan. 18, 2012, which is a national phase filing of International Patent Application No. PCT/GB2010/000781, filed Apr. 19, 2010, which claims priority to GB Application No. 0906643.2, filed Apr. 17, 2009; and GB Application No. 0907785.0, filed May 7, 2009, the contents of which are hereby incorporated by reference in its entirety.

FIELD OF THE INVENTION

The present invention relates to the field of detecting micro-organisms, in particular distinguishing between infection by bacteria or fungi and yeasts. The methods of the invention are highly sensitive and have numerous applications. Methods and kits are described which rely upon novel indicators of microorganism viability.

BACKGROUND TO THE INVENTION

There is a need for rapid detection of bacteria and fungi in clinical specimens and there is a requirement to distinguish between a bacterial and fungal infection. Culture approaches can be used but such techniques require several days to complete, especially when attempting to detect small numbers of bacteria and also when detecting slower growing micro organisms.

Tests may be carried out based upon measuring the presence of a molecule which can be linked to the presence in the sample of a bacterial or fungal cell. The most commonly detected molecule is Adenosine Triphosphate (ATP). Detection of DNA and RNA has also been proposed, although the correlation between the presence of DNA and RNA and viability is not clear-cut due to the variable persistence of nucleic acids in specimens post death of the microorganism (Keer & Birch, Journal of Microbiological Methods 53 (2003) 175-183). Detection of adenylate kinase as an indicator of viability has also been proposed (Squirrel) D J, Murphy M J, Leslie R L, Green J C D: A comparison of ATP and adenylate kinase as bacterial cell markers: correlation with agar plate counts. In Bioluminescence and chemiluminescence progress and current applications. Edited by: Stanley R A, Kricka L J. John Wiley and Sons; 2002 and WO 96/02665)

A routinely employed method for determining ATP levels involves the use of bioluminescence. The method uses the ATP dependency of the reaction in which light emitting luciferase catalyzes oxidation of luciferin. The method may be used to measure relatively low concentrations of ATP. Kits useful for detecting ATP using bioluminescence are commercially available from Roche, New Horizons Diagnostics Corp, Celsis etc.

Ligases are enzymes which catalyze ligation of nucleic acid molecules. The ligation reaction requires either ATP or NAD+ as co-factor depending upon the ligase concerned. WO 2009/007719 describes the use of NAD ligases to detect viable bacteria.

SUMMARY OF THE INVENTION

The present invention describes a procedure for detecting ligase expressing microorganisms, such as fungi (and bacteria) in a sample, such as a mammalian specimen or sample containing mammalian cells, by measuring the (ATP-dependent and/or NAD-dependent) ligase present in the sample after lysis of any fungal cells present, typically following a background reduction step to remove mammalian ATP-dependent ligase activity. The invention also describes a procedure for distinguishing between fungal and bacterial cells by measuring both the NAD-dependent ligase content in a sample and the ATP-dependent ligase content. If only ATP-dependent ligase is present then only fungal cells are present, if both enzyme activities are present then a mixed population of bacterial/fungal cells are present. If only NAD-dependent ligase activity is present the sample contains bacterial cells only.

In a first aspect, the invention provides a method of detecting a ligase expressing micro-organism in a sample comprising:
(a) treating the sample under conditions that inhibit the activity of ATP-dependent ligase from mammalian cells but which do not inhibit the activity of the microbial ligases,
(b) contacting the sample or a portion of the sample with a nucleic acid molecule which acts as a substrate for ligase activity in the sample,
(c) incubating the thus contacted sample under conditions suitable for ligase activity; and
(d) specifically determining the presence and/or the amount of a ligated nucleic acid molecule resulting from the action of the ligase on the substrate nucleic acid molecule to indicate the presence of the ligase expressing micro-organism.

In certain embodiments, the ligase expressing micro-organism comprises fungal or bacterial cells or both. The ligase expressed by the micro-organism may thus comprise an ATP-dependent ligase, an NAD-dependent ligase or both depending upon the cell types present in the sample. The presence of NAD-dependent ligase activity in the sample indicates the presence of bacterial cells (in particular eubacterial cells). Employment of suitable conditions in the sample, or a portion thereof, may permit NAD and ATP-dependent ligase activity to be determined respectively, as discussed herein.

The invention also provides a method of detecting an ATP-dependent ligase expressing micro-organism in a sample comprising:
(a) contacting the sample or a portion of the sample with a nucleic acid molecule which acts as a substrate for ATP-dependent ligase activity in the sample,
(b) incubating the thus contacted sample under conditions suitable for ATP-dependent ligase activity; and
(c) specifically determining the presence and/or the amount of a ligated nucleic acid molecule resulting from the action of the ATP-dependent ligase on the substrate nucleic acid molecule to indicate the presence of the ATP-dependent ligase expressing micro-organism.

In specific embodiments, the ATP-dependent ligase expressing micro-organism comprises fungal or bacterial cells or both. In preferred embodiments, the methods further comprise, prior to step (a), treating the sample under conditions that inhibit the activity of ATP-dependent ligase from mammalian cells but which do not inhibit the activity of the microbial ATP-dependent ligases. Suitable conditions are discussed in detail herein. These methods may additionally comprise:
(d) contacting the sample or a portion of the sample with a nucleic acid molecule which acts as a substrate for NAD-dependent ligase activity in the sample, (e) incubating the thus contacted sample under conditions suitable for NAD-dependent ligase activity; and
(f) specifically determining the presence (and/or the amount) of a ligated nucleic acid molecule resulting from the action of the NAD-dependent ligase on the substrate nucleic acid molecule to indicate the presence of bacterial cells in the sample.

In such methods, the presence of ATP-dependent ligase activity and absence of NAD-dependent ligase activity in the sample indicates that the sample contains fungal cells or a non-bacterial micro-organism. In certain embodiments, for example where no discrimination is needed between bacterial or fungal cells in the sample, the same nucleic acid molecule may be used as a substrate for both NAD-dependent ligase activity and ATP-dependent ligase activity.

Accordingly, the invention provides a method of detecting fungal or bacterial cells or both comprising:
(a) contacting the sample with a nucleic acid molecule which acts as a substrate for ATP-dependent ligase activity in the sample,
(b) incubating the thus contacted sample under conditions suitable for ATP-dependent ligase activity; and
(c) specifically determining the presence (and/or the amount) of a ligated nucleic acid molecule resulting from the action of the ATP-dependent ligase on the substrate nucleic acid molecule to indicate the presence of fungi and/or bacteria
(d) contacting the sample with a nucleic acid molecule which acts as a substrate for NAD-dependent ligase activity in the sample, which may be the same nucleic acid molecule as is used as the substrate for ATP ligase
(e) incubating the thus contacted sample under conditions suitable for NAD-dependent ligase activity; and
(f) specifically determining the presence (and/or the amount) of a ligated nucleic acid molecule resulting from the action of the NAD-dependent ligase on the substrate nucleic acid molecule to indicate the presence of bacteria only The invention also provides a method of distinguishing fungal cells from bacterial cells present in a sample with inhibition of the mammalian background from ATP-dependent ligase prior to lysis of the fungal and bacterial cells and detecting the released fungal ATP-dependent ligase or the released bacterial NAD-dependent ligase.

Accordingly, in a further aspect the invention provides a method of detecting fungal or bacterial cells or both comprising:
(a) treating the sample under conditions that inhibit the mammalian background signal from ATP-dependent ligase but which do not affect fungal ATP and microbial NAD-dependent ligases
(b) lysing the sample to release the fungal ATP and bacterial NAD-dependent ligases
(c) contacting the sample with a nucleic acid molecule which acts as a substrate for ATP-dependent ligase activity in the sample,
(d) incubating the thus contacted sample under conditions suitable for ATP-dependent ligase activity; and
(e) specifically determining the presence (and/or the amount) of a ligated nucleic acid molecule resulting from the action of the ATP-dependent ligase on the substrate nucleic acid molecule to indicate the presence of fungi and/or bacteria
(f) contacting the sample with a nucleic acid molecule which acts as a substrate for NAD-dependent ligase activity in the sample,
(g) incubating the thus contacted sample under conditions suitable for NAD-dependent ligase activity; and
(h) specifically determining the presence (and/or the amount) of a ligated nucleic acid molecule resulting from the action of the NAD-dependent ligase on the substrate nucleic acid molecule to indicate the presence of bacteria only A "sample" in the context of the present invention is defined to include any sample in which it is desirable to test for the presence of either bacteria expressing an NAD-dependent ligase or fungi expressing an ATP-dependent ligase or both. Thus, the sample is generally a sample suspected of containing, or in some circumstances known to contain, a micro-organism. Detection of ligase activity in the sample is considered indicative of the presence of the micro-organism. The sample is generally one that may contain mammalian cells, which also express ligase activity. However, the methods of the invention permit ligase activity in the sample resulting from the presence of mammalian cells to be selectively removed (through inactivation) prior to detection of microbial ligase activity. The step of removing any mammalian cell ATP-dependent ligase activity may not be necessary in samples where it is known that no mammalian cells are present. This may be the case for example where NAD versus ATP dependent ligase activity is investigated to determine whether fungal and/or bacterial cells are present in the sample.

Thus the sample may comprise, consist essentially of or consist of a clinical sample, or an in vitro assay system for example. Samples may comprise, consist essentially of or consist of beverage or food samples or preparations thereof, or pharmaceutical or cosmetic products such as personal care products including shampoos, conditioners, moisturisers etc., all of which are tested for microbial contamination as a matter of routine. The sample may comprise, consist essentially of or consist of tissue or cells and may comprise, consist essentially of or consist of a sputum or a blood sample or a platelet sample for example.

By "ATP-dependent ligase" is meant an ATP ligase which depends upon the adenosine triphosphate (ATP) cofactor for activity. The activity of the ATP-dependent ligase is the formation of a phosphodiester bond between the 5' end of a nucleic acid molecule and the 3' end of a nucleic acid molecule. By "NAD-dependent ligase" is meant a DNA ligase which depends upon the nicotinamide adenine dinucleotide (NAD+) cofactor for activity. NAD-dependent ligases can be distinguished from ATP-dependent ligases which rely upon the cofactor ATP for activity. The activity of the NAD-dependent ligase is the formation of a phosphodiester bond between the 5' end of a nucleic acid molecule and the 3' end of a nucleic acid molecule.

The methods of the present invention provide significant technical advantages, due in large part to the fact that a novel nucleic acid molecule is generated as part of the method. In the methods of the present invention, unreacted nucleic acid molecule will not contribute to the signal, and as a result no false positive signals should be produced when the methods are carried out.

Furthermore, the method is highly sensitive providing detection of the ATP and NAD-dependent ligases present in the sample down to femtogram and possibly even attogram levels. The sensitivity is derived from the fact that every bacterial or fungal cell contains thousands of enzyme molecules, and thus each can catalyse multiple ligation events under suitable conditions. Every bacterial and fungal cell must produce ligase activity to repair ongoing genomic damage and this essential activity contributes to its usefulness as a marker for the presence of viable microbial cells. Thus unlike PCR approaches, which must target one or a few copies of a gene per cell or use additional steps or reagents to detect ribosomal or messenger RNA, the approach described herein targets the detection of multiple copies of the ATP and NAD-dependent ligase per cell in a simple assay format. The sensitivity is further enhanced compared to other approaches in that each copy of the ligase is able to modify multiple (hundreds or thousands) substrate nucleic acid molecules which can each then be detected.

Depending on the sample type which may contain host ATP dependent ligases it may be beneficial to inactivate these host ligases by pretreating the sample in such a way that the host ligases are inactivated but the fungal or bacterial ligases remain active. The approach described herein may, in certain embodiments, rely on the difference in structure of mammalian cells and bacterial or fungal cells. Conditions are described that lyse or solubilise the mammalian cell membrane but courtesy of the fungal and bacterial cell walls, leave the fungal and bacterial membranes intact. Once the ligases are released from the mammalian cells they are exposed to conditions that further inactivate these released ligases. Conditions used for lysis of the mammalian membranes include the use of detergents that may or may not be used in conjunction with high or low pH. Conditions used for the inactivation of released ligases include the use of high or low pH.

Thus, in certain embodiments the methods of the invention comprise treatment of the sample with an agent that permeabilizes the cell membrane of mammalian cells in the sample. The agent preferably does not significantly permeate the cell wall of any micro-organisms in the sample. The agent may be a detergent, many suitable examples of which are known in the art and commercially available. One specific example shown to be effective herein is the surfactant/detergent Triton X-100.

As indicated above, the conditions that inhibit the activity of ATP-dependent ligase from mammalian cells but which do not inhibit the activity of the microbial ligases may comprise high or low pH. High pH is generally a pH of at least around 10, such as around 10, 11, 12, 13 or 14. Low pH is generally a pH of less than or equal to around 4, such as around 4, 3, 2, or 1. Altering the pH of the sample may be achieved using any suitable means, as would be readily appreciated by one skilled in the art. It is shown herein that microbial ligases are surprisingly resistant to extremes of pH, whereas mammalian ligases are inactivated under the same pH conditions. This permits selective detection of microbial ligases in a sample containing both mammalian cells and microbial cells. In specific embodiments, the conditions that inhibit the activity of ATP-dependent ligase from mammalian cells but which do not inhibit the activity of the microbial ligases comprise treating the sample with sodium hydroxide (NaOH) or sodium carbonate (Na2CO3). Such agents can readily be used, as shown herein, to increase the pH of the sample to high pH thus inactivating mammalian ligase activity whilst leaving the microbial (fungal and bacterial) ligases active. Suitable concentrations and volumes of the appropriate agent can be applied by a skilled person. In certain embodiments, however, the NaOH is around 5 mM NaOH. In further embodiments, the pH is around 12 to inactivate mammalian ATP-dependent ligase activity (but not microbial ligases). In yet further embodiments, the treatment is carried out for around 20 minutes. Suitable agents for lowering the pH to less than or equal to around 4 include acids such as hydrochloric acid (HCl) and sulphuric acid (H2SO4).

In specific embodiments, pH conditions may be increased to at least around 11, or at least around 11.2. This treatment may result in lysis of micro-organisms in the sample and thus lead to ligase release into the sample. This permits detection of ligases in the sample, originating from the micro-organism, without the need for a separate cell lysis step. Under these conditions, mammalian ligases (such as blood ATP-dependent ligases) are inactivated.

In other embodiments, the methods of the invention further comprise lysis of micro-organisms (fungi or bacteria) in the sample to release ATP and NAD-dependent ligase. This step is preferably carried out before the sample is contacted with the nucleic acid substrate, although this is not essential. Thus, the methods of the invention may further comprise, following the treatment step, lysing the sample to release the microbial ligase. However, as shown herein, microbial ligases are much more resistant to high pH conditions than mammalian ligases. Thus, the methods of the invention may incorporate a lysis step to lyse all cells in the sample, irrespective of their origin (i.e. to include both micro-organisms and mammalian cells). Following this lysis step, the mammalian ligases can be selectively inactivated, for example using high or low pH conditions, and the ligases expressed by any micro-organisms in the sample detected according to the methods of the invention.

In specific embodiments, lysis is performed mechanically, although lysis may also be performed chemically. Suitable agents for lysing bacterial and fungal cells selectively are known in the art and include bacterial protein extraction reagents such as B-PER (Pierce) and Y-PER (Pierce) for example. Mechanical be achieved through sonication or French Press or ribolysis ('bead beating') for example. However, lysis may not be essential in all embodiments of the invention. In particular, increasing the permeability of the bacterial or fungal cell wall and/or membrane may in certain embodiments be sufficient to enable detection of ATP or NAD-dependent ligase activity according to the methods of the invention. Suitable agents and techniques for achieving this increase in permeability are known in the art and include high pH conditions as described herein.

As stated herein, one step in the ligase assay methods of the invention comprises, consists essentially of or consists of contacting the sample with a nucleic acid molecule which acts as a substrate for microbial (ATP or NAD-dependent) ligase activity in the sample. Any suitable ligatable molecule which can be specifically detected once ligated may be utilised in the methods of the invention.

For the avoidance of doubt, it is hereby stated that the ligated nucleic acid molecule is generally a novel detectable nucleic acid molecule which has a different overall structure to that of the original (substrate) nucleic acid molecule. Thus, the novel detectable nucleic acid molecule may contain additional nucleotides such that the novel nucleic acid molecule may be uniquely identified, for example by amplification utilising primers which can only bind and produce an amplification product using the ligated nucleic acid molecule as a template. However, it may be that only one strand is extended as compared to the (original) substrate nucleic acid molecule, for example the ligase may seal a nick in one strand of a double stranded substrate molecule.

The substrate nucleic acid molecules for use in the methods, and inclusion in the kits, of the invention, must be of sequence and structure such that the ATP or NAD-dependent ligase can act on the molecule as the case may be to produce detectable ligated (novel) nucleic acid molecule.

Suitable substrate nucleic acid molecules for use in the invention comprise, consist essentially of or consist of the nucleotide sequences set forth as SEQ ID NO: 1, 2 and 3 and SEQ ID NO: 6, 7, and 8 respectively and described in more detail in the experimental section below. It is noted that variants of these sequences may be utilised in the present invention. For example, additional flanking sequences may be added. Variant sequences may have at least 90%, at least 91%, at least 92%, at least 93%, at least 94%, at least 95%, at least 96%, at least 97%, at least 98%, or at least 99% nucleotide sequence identity with the nucleotide sequences of the substrate nucleic acid. The nucleic acid molecules may incorporate synthetic nucleotide analogues as appropriate or may be RNA or PNA based for example, or mixtures thereof. They may be labelled, such as using a fluorescent label, or FRET pair, in certain embodiments to facilitate detection. Suitable detection methods are described herein.

"Nucleic acid" is defined herein to include any natural nucleic acid and natural or synthetic analogues that are capable of being ligated by an ATP or NAD-dependent ligase in order to generate a ligated (novel detectable) nucleic acid molecule. The ligation reaction may involve either joining of two DNA molecules or sealing a nick in a nucleic acid molecule to produce a detectable ligated nucleic acid molecule for example. Suitable nucleic acid molecules may be composed of, for example, double or single-stranded DNA and double or single-stranded RNA. Nucleic acid molecules which are partially double-stranded and partially single-stranded are also contemplated in certain embodiments of the invention. In certain embodiments the substrate nucleic acid molecule comprises, consists essentially of or consists of dsDNA, to include nicked dsDNA. The term "nucleic acid" encompasses synthetic analogues which are capable of being ligated by ATP or NAD-dependent ligase in a sample in an analogous manner to natural nucleic acids, for example nucleic acid analogues incorporating non-natural or derivatized bases, or nucleic acid analogues having a modified backbone. In particular, the term "double-stranded DNA" or "dsDNA" is to be interpreted as encompassing dsDNA containing non-natural bases.

Though the nucleic acid substrate may comprise, consist essentially of or consist of a blunt-ended double-stranded DNA molecule, in a separate embodiment the nucleic acid substrate for the ATP or NAD-dependent ligase comprises, consists essentially of or consists of two double stranded DNA molecules with a complementary overhang and 5' phosphate groups at the ends to be joined. In one specific embodiment, the complementary overhang is between 2 and 10, such as 3 or 5 base pairs. In an alternative embodiment, the nucleic acid substrate comprises, consists essentially of or consists of a partially double-stranded DNA molecule with a nick containing a 5' phosphate. Synthesized nucleic acid molecules are commercially available and can be made to order with a terminal 5' phosphate group attached. This has the technical advantage that 100% of the nucleic acid molecules used in the methods of the invention will be labelled with a 5' phosphate group. Furthermore, the nucleic acid substrates can be designed to specification, for example to include biotin molecules for subsequent post-ligation capture if so desired, as described herein.

Thus, in embodiments of the invention, the novel nucleic acid molecule that is detected is generated by ligation of the 3' end of the nucleic acid molecule to the 5' end of a further nucleic acid molecule. In these embodiments, if the ligase is present in the sample, it will catalyse the ligation and a ligated nucleic acid molecule (incorporating an overall novel sequence) will be formed which can be detected by a subsequent process, as detailed herein (such as a nucleic acid amplification process for example).

Thus, the substrate nucleic acid molecule may, in fact, comprise, consist essentially of or consist of two or more nucleic acid molecules as appropriate. This applies generally to the methods and kits of the invention.

In certain embodiments, the nucleic acid substrate comprises, consists essentially of or consists of two double stranded nucleic acid molecules with single-stranded complementary overhangs.

The 3' end of nucleic acid substrate molecules that are not productively joined in terms of producing a ligated product which is then detected (desired to be joined) may be blocked with a suitable blocking group in order to ensure that they cannot participate in a ligation reaction. Any appropriate blocking group may be utilised.

In specific embodiments, the nucleic acid molecule which acts as a substrate for ATP or NAD-dependent ligase activity in the sample comprises, consists essentially of or consists of a nicked double stranded nucleic acid molecule. In specific embodiments, the overall substrate may be made up of three specific single stranded DNA (ssDNA) molecules. Two or more of the ssDNA molecules may be of identical sequence. One ssDNA molecule may hybridize to the other two nucleic acid molecules in a manner such that a double stranded region is formed that contains a nick. NAD-dependent ligase activity, if present in the sample, may seal the nick thus producing a double stranded DNA molecule which can be detected according to the methods described herein.

In further specific embodiments, the nucleic acid molecule which acts as a substrate for ATP or NAD-dependent ligase activity in the sample comprises, consists essentially of or consists of two nucleic acid molecules which can be ligated together.

Preferably, the nucleic acid substrate is present in excess, and in particular in large molar excess, over the ligase in the sample. This is an important technical distinction over prior art methods. Because a novel ligated nucleic acid molecule is detected, only the presence of this molecule in the sample is essential for the detection methods to work effectively. Thus, it is not detrimental to the methods of the invention if other nucleic acid molecules are present in the sample such as from the bacteria or fungi to be detected or from mammalian sources which may be found in the sample to be tested for example.

Preferably, the substrate nucleic acid molecules are designed such that they do not have high levels of homology with the genome of the one or more bacteria or other micro-organisms which produce the ATP or NAD-dependent ligase which is to be detected in the sample. This means that, even in the presence of contaminating nucleic acid molecules, only the novel ligated nucleic acid molecule may be detected. Thus, the substrate should have sufficiently low levels of sequence identity with the genomic DNA of the bacteria or fungi to be detected to prevent non-specific amplification of genomic DNA producing a false positive result. The sequence of the substrate may thus be designed with the target bacteria in mind. In particular, the primers for amplifying specifically the novel ligated nucleic acid molecule are designed such that they do not produce an amplification product from the bacterial genomic DNA. For example, the substrate and primers may incorporate complementary non-naturally occurring molecules which can base pair with each other, and allow specific amplification of bacterial genomic DNA. As an example, pyDAD and puADA may be incorporated into primers and substrate molecules as appropriate (Sismour et al., Nucleic Acids Research, 2004, Vol. 32, No. 2: 728-735).

Preferably, the homology is less than about 5%, less than about 10%, less than about 12.5%, less than about 15%, less than about 20%, less than about 30%, less than about 40%, 50%, 60%, 70% or 80% sequence identity with the corresponding nucleotide sequence from the one or more bacteria or other micro-organisms which produce the ATP or NAD-dependent ligase which is to be detected in the sample. In one embodiment, there is no sequence identity with the corresponding nucleotide sequence from the one or more bacteria or other micro-organisms which produce the ATP or NAD-dependent ligase which is to be detected in the sample over approximately 10, 20, 30, 40 or 50 contiguous nucleotides. In another embodiment, there is less than about 10% or less than about 12.5%, 15%, 20%, 30%, 40%, 50% or 60% sequence identity over approximately 10, 20, 30, 40 or 50 contiguous nucleotides with the corresponding nucleotide sequence from the one or more bacteria or other micro-organisms which produce the ATP or NAD-dependent ligase which is to be detected in the sample.

A further step of the methods of the invention comprises, consists essentially of or consists of incubating the sample under conditions suitable for ATP and/or NAD-dependent ligase activity. Any suitable conditions may be employed, as would be readily determined by one of skill in the art. For example ligation may occur at any temperature between around 4 and 80° C. depending upon the ligase concerned (thermophilic bacteria may be detected using reactions incubated at higher temperatures than mesophilic bacteria for example). Preferred incubation temperatures are between around 4 and 40° C., more preferably between around 20 and 37° C. and most preferably at room temperature for general (viable) bacterial or fungal detection. Suitable incubation times may be between approximately 10 minutes and 10 hours, such as between around 30 minutes, 1 hour or 2 hours and 5, 6, 7, 8 or 9 hours. Incubation may occur in a suitable buffer. Commercially available ligase buffers include E. coli ligase buffer available from NEB. Suitable incubation conditions for use of a ligase are well known in the art and are recommended with commercially available ligases. A suitable cofactor may be added to the sample in order to facilitate detection of the appropriate microbial ligase. For fungal cells this may be ATP, whereas for bacterial cells NAD may be added.

In embodiments where the sample is assessed to distinguish between the presence of NAD-dependent ligase expressing bacteria (in particular eubacteria) and ATP-dependent ligase expressing fungi the conditions may be altered to permit detection of the respective ligase activities. This may involve splitting the sample and testing for NAD-dependent ligase activity specifically in one portion of the sample and for ATP-dependent ligase activity specifically in another, or the other, portion of the sample. The splitting may occur before or after the step of treating the sample under conditions that inhibit the activity of ATP-dependent ligase from mammalian cells but which do not inhibit the activity of the microbial ligases. In each respective sample, only the appropriate cofactor (ATP or NAD) may be added to permit any suitable ligase activity in that sample to be detected. The absence of the essential cofactor should prevent the other ligase from being detected. If required, the sample portion may be depleted of any endogenous cofactor prior to testing for ligase activity. For example luciferase may be added to a sample to deplete the sample of ATP. Suitable enzymes such as oxidoreductases may be used to deplete the sample of NAD prior to ligase detection.

The methods of the invention may incorporate suitable controls. This may be useful in conjunction with certain sensitive detection techniques, such as nucleic acid amplification techniques (as described herein) to ensure that accurate results have been obtained. For example, the controls may incorporate testing a sample in which microbial (ATP and/or NAD-dependent) ligase activity is known to be present. If no ligated nucleic acid molecule is produced when the substrate is added to this sample, it is clear there is a problem for example with the reagents used in the methods or with the detection technique. A suitable negative control may be a sample in which there is known to be no ATP or NAD-dependent ligase activity. Again, a positive result/detection of similar levels of product as are found in the test sample is an indication that there is a problem. A control in which no nucleic acid based substrate molecule is added may also be employed to ensure the methods are not detecting an unrelated ligation event. All combinations and permutations of appropriate controls are envisaged in the present invention. Suitable controls for use in nucleic acid amplification reactions are employed in specific embodiments of the invention, as described herein.

In preferred embodiments of the invention, the novel nucleic acid molecule, produced according to the presence of microbial (ATP or NAD-dependent) ligase activity in the sample (as an indicator of the presence of one or more (viable) micro-organisms, in particular fungi and/or bacteria in the sample), is detected using nucleic acid amplification techniques.

This serves to make the methods of the invention maximally sensitive. Such amplification techniques are well known in the art, and include methods such as PCR, NASBA (Compton, 1991), 3SR (Fahy et al., 1991), Rolling circle replication, Transcription Mediated Amplification (TMA), strand displacement amplification (SDA) Clinical Chemistry 45: 777-784, 1999, the DNA oligomer self-assembly processes described in U.S. Pat. No. 6,261,846 (incorporated herein by reference), ligase chain reaction (LCR) (Barringer et al., 1990), selective amplification of target polynucleotide sequences (U.S. Pat. No. 6,410,276), arbitrarily primed PCR (WO 90/06995), consensus sequence primed PCR (U.S. Pat. No. 4,437,975), invader technology, strand displacement technology and nick displacement amplification (WO 2004/067726). The list above is not intended to be exhaustive. Any nucleic acid amplification technique may be used provided the appropriate nucleic acid product is specifically amplified.

Amplification is achieved with the use of amplification primers specific for the sequence of the novel/ligated nucleic acid molecule which is to be detected. In order to provide specificity for the nucleic acid molecules primer binding sites corresponding to a suitable region of the sequence may be selected. The skilled reader will appreciate that the nucleic acid molecules may also include sequences other than primer binding sites which are required for detection of the novel nucleic acid molecule produced by the NAD-dependent ligase activity in the sample, for example RNA Polymerase binding sites or promoter sequences may be required for isothermal amplification technologies, such as NASBA, 3SR and TMA.

One or more primer binding sites may bridge the ligation boundary of the substrate nucleic acid molecule such that an amplification product is only generated if ligation has occurred, for example. Alternatively, primers may bind either side of the ligation boundary and direct amplification across the boundary such that an amplification product is only generated (exponentially) if the ligated nucleic acid molecule is formed. As discussed above, primers and the substrate nucleic acid molecule(s) may be designed to avoid non-specific amplification of bacterial genomic DNA.

Suitable primers for use in the methods of the invention comprise, consist essentially of or consist of the nucleotide sequences set forth as SEQ ID NO: 4 and 5 and SEQ ID NO: 9 and 10 and are described in more detail in the experimental section below. These primers form a separate aspect of the invention. It is noted that variants of these sequences may be utilised in the present invention. In particular, additional sequence specific flanking sequences may be added, for example to improve binding specificity, as required. Variant sequences may have at least 90%, at least 91%, at least 92%, at least 93%, at least 94%, at least 95%, at least 96%, at least 97%, at least 98%, or at least 99% nucleotide sequence identity with the nucleotide sequences of the primers set forth in the example. The primers may incorporate synthetic nucleotide analogues as appropriate or may be RNA or PNA based for example, or mixtures thereof. The primers may be labelled, such as with fluorescent labels and/or FRET pairs, depending upon the mode of detection employed. Probes may be utilised, again which may be labelled, as desired.

Thus, in certain aspects, the methods of the invention are carried out using nucleic acid amplification techniques in order to detect the novel nucleic acid molecule produced as a direct result of the action of ATP or NAD-dependent ligase activity on the substrate nucleic acid molecule which indicates the presence of a bacterial cell or other NAD-dependent ligase expressing micro-organism in the sample. In certain embodiments the technique used is selected from PCR, NASBA, 3SR, TMA, SDA and DNA oligomer self-assembly.

Detection of the amplification products may be by routine methods, such as, for example, gel electrophoresis but is preferably carried out using real-time or end-point detection methods.

A number of techniques for real-time or end-point detection of the products of an amplification reaction are known in the art. These include use of intercalating fluorescent dyes such as SYBR Green I (Sambrook and Russell, Molecular Cloning—A Laboratory Manual, Third edition), which allows the yield of amplified DNA to be estimated based upon the amount of fluorescence produced. Many of the real-time detection methods produce a fluorescent read-out that may be continuously monitored; specific examples including molecular beacons and fluorescent resonance energy transfer probes. Real-time and end-point techniques are advantageous because they keep the reaction in a "single tube". This means there is no need for downstream analysis in order to obtain results, leading to more rapidly obtained results. Furthermore keeping the reaction in a "single tube" environment reduces the risk of cross contamination and allows a quantitative output from the methods of the invention. This may be particularly important in the context of the present invention where health and safety concerns may be of paramount importance (such as in detecting potential bacterial contamination of platelet samples for example).

Real-time and end-point quantitation of PCR reactions may be accomplished using the TaqMan® system (Applied Biosystems), see Holland et al; Detection of specific polymerase chain reaction product by utilising the 5'-3' exonuclease activity of *Thermus aquaticus* DNA polymerase; Proc. Natl. Acad. Sci. USA 88, 7276-7280 (1991), Gelmini et al. Quantitative polymerase chain reaction-based homogeneous assay with flurogenic probes to measure C-Erb-2 oncogene amplification. Clin. Chem. 43, 752-758 (1997) and Livak et al. Towards fully automated genome wide polymorphism screening. Nat. Genet. 9, 341-342 (19995) (incorporated herein by reference). This type of probe may be generically referred to as a hydrolytic probe. Suitable hydrolytic/Taqman probes for use in real time or end point detection are also provided. They may comprise, consist essentially of or consist of the nucleotide sequence set forth as SEQ ID NO: 11. The probe is suitably labelled, for example using the labels detailed below.

In the Molecular Beacon system, see Tyagi & Kramer. Molecular beacons—probes that fluoresce upon hybridization. Nat. Biotechnol. 14, 303-308 (1996) and Tyagi et al. Multicolor molecular beacons for allele discrimination. Nat. Biotechnol. 16, 49-53 (1998) (incorporated herein by reference), the beacons are hairpin-shaped probes with an internally quenched fluorophore whose fluorescence is restored when bound to its target. These probes may be referred to as hairpin probes.

A further real-time fluorescence based system which may be incorporated in the methods of the invention is Zeneca's Scorpion system, see Detection of PCR products using self-probing amplicons and fluorescence by Whitcombe et al. Nature Biotechnology 17, 804-807 (1 Aug. 1999). Additional real-time or end-point detection techniques which are well known to those skilled in the art and which are commercially available include Lightcycler® technology, Amplifluour® primer technology, DzyNA primers (Todd et al., Clinical Chemistry 46:5, 625-630 (2000)), or the Plexor™ qPCR and qRT-PCR Systems.

Thus, in further aspects of the invention the products of nucleic acid amplification are detected using real-time or end point techniques. In specific embodiments of the invention the real-time technique consists of using any one of hydrolytic probes (the Taqman® system), FRET probes (Lightcycler® system), hairpin primers (Amplifluour® system), hairpin probes (the Molecular beacons system), hairpin probes incorporated into a primer (the Scorpion® probe system), primers incorporating the complementary sequence of a DNAzyme and a cleavable fluorescent DNAzyme substrate (DzYNA), Plexor qPCR and oligonucleotide blocking systems.

In certain embodiments, the reaction mixture will contain all of; the sample under test, the substrate nucleic acid molecule(s), reagents, buffers and enzymes required for amplification of the novel (ligated) nucleic acid molecule optionally in addition to the reagents required to allow real time or end-point detection of amplification products. Thus the entire detection method for the ATP or NAD-dependent ligase (from the one or more bacterial cells or fungi of interest) may occur in a single reaction, with a quantitative output, and without the need for any intermediate washing steps. Use of a "single tube" reaction is advantageous because there is no need for downstream analysis in order to obtain results, leading to more rapidly obtained results. Furthermore keeping the reaction in a "single tube" environment reduces the risk of cross contamination and allows a quantitative output from the methods of the invention. Also, single tube reactions are more amenable to automation, for example in a high throughput context.

Alternatively, the methods of the invention may be carried out in step-wise fashion. Thus, in a first step it may first be necessary to prepare the sample in a form suitable for use in the method of the invention. For example, as discussed herein, selective cell lysis or increasing cellular permeability may be required.

The methods of the invention may also prove to have diagnostic utility, whereby an infection may be specifically and sensitively detected in the early stages when only minimal levels of the infecting bacterial or fungal cells expressing an ATP or NAD-dependent ligase are present and it is desired to determine which type of organism is active in the infection. Thus, the methods of the invention may be used to diagnose the micro-organism responsible for an infection, or a disease associated with the presence of a micro-organism. All aspects of the invention and steps of the method as described herein are therefore applicable to a method of diagnosing the organism responsible for an infection, or a disease associated with the presence of a micro-organism, such as a bacterial or fungal cell.

Therefore, in one specific further aspect there is provided a method of diagnosing the organism responsible for an infection, or a disease associated with the presence of a bacterial or fungal cell, comprising, consisting essentially of or consisting of the steps of, in a sample obtained from the subject:
(a) contacting the sample with a nucleic acid molecule which acts as a substrate for ATP-dependent ligase activity in the sample,
(b) incubating the thus contacted sample under conditions suitable for ATP-dependent ligase activity; and
(c) specifically determining the presence (and/or the amount) of a ligated nucleic acid molecule resulting from the action of the ATP-dependent ligase on the substrate nucleic acid molecule to indicate the presence of fungi and/or bacteria causing the infection The method may additionally comprise:
(d) contacting the sample with a nucleic acid molecule which acts as a substrate for NAD-dependent ligase activity in the sample,
(e) incubating the thus contacted sample under conditions suitable for NAD-dependent ligase activity; and
(f) specifically determining the presence (and/or the amount) of a ligated nucleic acid molecule resulting from the action of the NAD-dependent ligase on the substrate nucleic acid molecule to indicate the presence of bacteria only causing the infection.

Similarly, there is provided a method of diagnosing the organism responsible for an infection, or a disease associated with the presence of a bacterial or fungal cell, comprising, consisting essentially of or consisting of the steps of, in a sample obtained from the subject:
(a) treating the sample under conditions that inhibit the mammalian background from ATP-dependent ligase but which do not affect microbial ATP and NAD-dependent ligases
(b) lysing the sample to release the microbial ATP and NAD-dependent ligases
(c) contacting the sample with a nucleic acid molecule which acts as a substrate for ATP-dependent ligase activity in the sample, The method may additionally comprise:
(d) incubating the thus contacted sample under conditions suitable for ATP-dependent ligase activity; and
(e) specifically determining the presence (and/or the amount) of a ligated nucleic acid molecule resulting from the action of the ATP-dependent ligase on the substrate nucleic acid molecule to indicate the presence of fungi and/or bacteria causing the infection
(f) contacting the sample with a nucleic acid molecule which acts as a substrate for NAD-dependent ligase activity in the sample,
(g) incubating the thus contacted sample under conditions suitable for NAD-dependent ligase activity; and
(h) specifically determining the presence (and/or the amount) of a ligated nucleic acid molecule resulting from the action of the NAD-dependent ligase on the substrate nucleic acid molecule to indicate the presence of bacteria only causing the infection.

In this context the "sample" will generally be a clinical sample. The sample being used will depend on the condition that is being tested for. Typical samples which may be used, but which are not intended to limit the invention, include whole blood, serum, plasma, platelet and urine samples etc. taken from a patient, most preferably a human patient. As mentioned above, the samples will contain mammalian cells. The methods of the invention permit mammalian cell ligase activity to be removed from the sample prior to detection of microbial ligase activity, thus enabling the methods to have diagnostic utility.

In a preferred embodiment, the test will be an in vitro test carried out on a sample removed from a subject.

In a further embodiment, the above-described diagnostic methods may additionally include the step of obtaining the sample from a subject. Methods of obtaining a suitable sample from a subject are well known in the art. Alternatively, the method may be carried out beginning with a sample that has already been isolated from the patient in a separate procedure. The diagnostic methods will most preferably be carried out on a sample from a human, but the method of the invention may have diagnostic utility for many animals.

The diagnostic methods of the invention may be used to complement any already available diagnostic techniques, potentially as a method of confirming an initial diagnosis. Alternatively, the methods may be used as a preliminary diagnosis method in their own right, since the methods provide a quick and convenient means of diagnosis. Furthermore, due to their inherent sensitivity, the diagnostic methods of the invention require only a minimal sample, thus preventing unnecessary invasive surgery. Also, a large but non-concentrated sample may also be tested effectively according to the methods of the invention.

Thus, the methods of the invention have multiple applications beyond detection of contaminating organisms in a sample. The description provided above with respect to the basic detection aspects of the invention apply mutatis mutandis to the further aspects of the invention and is not repeated for reasons of conciseness. For example, all steps of the methods and suitable controls may be incorporated into these methods of the invention.

In specific embodiments the microbial, more specifically NAD-dependent, ligase is derived from a pathogenic micro-organism, in particular a pathogenic bacterium.

The bacterium may be any bacterium which is capable of causing infection or disease in a subject, preferably a human subject. In one embodiment, the bacteria comprises or consists essentially of or consists of any one or more of *Staphylococcus* species, in particular *Staphylococcus aureus* and preferably methicillin resistant strains, *Enterococcus* species, *Streptococcus* species, *Mycobacterium* species, in particular *Mycobacterium tuberculosis*, *Vibrio* species, in particular *Vibrio cholerae*, *Salmonella* and/or *Escherichia coli* etc. The bacteria may comprise, consist essentially of or consist of *Clostridium* species and in particular *C. difficile* in certain embodiments. *C. difficile* is the major cause of antibiotic-associated diarrhoea and colitis, a healthcare associated intestinal infection that mostly affects elderly patients with other underlying diseases.

In specific embodiments the microbial, more specifically ATP-dependent, ligase is derived from pathogenic fungi. The fungi may be any fungi which are capable of causing infection or disease in a subject, preferably a human subject.

In one embodiment, the fungus comprise or consists essentially of or consists of any one or more of *Candida albicans, Candida glabrata, Candida tropicalis, Candida krusei, Candida parapsilosis, Aspergillus fumigatus, Cryptococcus neoformans, Histoplasma capsulatum* and *Pneumocystis jirovecii*.

Also provided are test kits for performing these methods of the invention. The test kit may be a disposable test kit in certain embodiments. Each component of the test kit may be supplied in a separate compartment or carrier, or one or more of the components may be combined—provided that the components can be stably stored together.

Thus, the invention provides a kit for use in the methods of the invention comprising:
(a) at least one nucleic acid molecule which acts as a substrate for microbial ligase activity in the sample
(b) means for inhibiting the activity of ATP-dependent ligase from mammalian cells which means do not inhibit the activity of the microbial ligases.

All aspects and embodiments of the methods of the invention apply mutatis mutandis to the kits of the invention. Thus, the means for inhibiting the activity of ATP-dependent ligase from mammalian cells which means do not inhibit the activity of the microbial ligases may comprise a suitable agent to alter the pH of the sample in which the reaction takes place. In particular embodiments, the agent comprises a high pH solution, although it may also comprise a low pH solution. In specific embodiments, the means for inhibiting the activity of ATP-dependent ligase from mammalian cells which means do not inhibit the activity of the microbial ATP-dependent ligases comprises, consists essentially of or consists of sodium hydroxide (NaOH) or sodium carbonate (Na2CO3) (to raise the pH) or hydrochloric acid (HCl) or sulphuric acid (H2SO4) (to lower the pH). The agent may be present in any suitable concentration or volume as would be readily appreciated by one skilled in the art. In one specific embodiment, the NaOH is 5 mM NaOH.

Treatment with suitable means for inhibiting the activity of ATP-dependent ligase from mammalian cells, as discussed herein, may require initially application of an agent to selectively permeate the cell membrane of mammalian cells. Thus, the kits of the invention may further comprise, consist essentially of or consist of an agent that permeabilizes the mammalian cell membrane but which does not permeate the cell wall of the micro-organism. Any suitable agent may be employed. In specific embodiments, the agent is a detergent, such as Triton X-100.

The kits may further comprising primers for specific detection of a ligated nucleic acid molecule produced by microbial ligase activity in the sample on the substrate nucleic acid molecule. Suitable primers comprise, consist essentially of or consist of the nucleotide sequences set forth as SEQ ID NO: 4 and 5 and SEQ ID NO: 9 and 10.

In further embodiments, the at least one nucleic acid molecule is immobilized on a solid support or is provided together with means for immobilizing the substrate nucleic acid molecule on said solid support. The immobilization of the substrate nucleic acid molecule on a solid support allows effective capture of the microbial ligase from the sample. The interaction of the immobilized substrate nucleic acid molecule with the ligase results in the generation of a novel, ligated nucleic acid molecule. Thus, the kits of the invention may further comprise a solid support. The substrate may or may not be provided pre-loaded on the solid support. If it is not pre-immobilized on the solid support, suitable reagents to allow immobilization may be provided in the kit, optionally together with suitable instructions. Reagents to allow immobilization would be well known to one of skill in the art. Any means of immobilization may be utilised provided that it does not have an adverse effect on the implementation of the methods of the invention, especially in terms of specificity and sensitivity of detection of the microbial ligase from the one or more target bacterial or fungal cells or micro-organisms.

Any suitable solid support may be included in the kits of the invention. The nature of the solid support is not critical to the performance of the invention provided that the substrate nucleic acid molecule may be immobilized thereon without adversely affecting microbial ligase activity, including the ability of the enzyme to interact with the nucleic acid molecule. Non-limiting examples of solid supports include any of beads, such as polystyrene beads and paramagnetic beads and derivatives thereof, affinity columns, microtitre plates etc. Where the substrate nucleic acid molecule is in fact two (or more) nucleic acid molecules which are ligated together, either one or both of the substrate nucleic acid molecules may be immobilized on a solid support. In specific embodiments, the separate substrate nucleic acid molecules may be immobilized on the same support as one another. This allows the molecules to be in proximity to ensure that ligation is efficient if the microbial (bacterial and/or fungal) ligase is present in the sample under test. Biotin and/or the streptavidin reagents may be incorporated in the kits to facilitate immobilisation for example.

The kit may also comprise means to facilitate lysis or to increase the permeability of the microbial cells in the sample, to permit microbial ligase activity to be detected. The discussion of suitable means herein applies mutatis mutandis to the kits of the invention. In one embodiment, the kit further comprises beads to facilitate lysis of microbial cells in the sample (through use of a bead-beater technique). In specific embodiments, the beads are around 1 mm in diameter to facilitate lysis of fungal cells. For lysis of bacterial cells, smaller beads, of around 100 μm may be employed. Thus the kit may include beads of a range of diameters in certain embodiments.

The kit may also incorporate reagents necessary for nucleic acid amplification. Employment of nucleic acid amplification techniques allows sensitive detection of the presence of a novel ligated nucleic acid molecule. Suitable techniques and the necessary reagents would be immediately apparent to one skilled in the art. Thus, the kits may in particular incorporate suitable primers for specific detection of the ligated nucleic acid molecule—as discussed in greater detail herein. The kits may also incorporate suitable reagents for real-time detection of amplification products.

The kits may incorporate a suitable carrier in which the reactions take place. Advantageously, such a carrier may comprise a multi-well plate, such as a 48 or 96 well plate for example. Such a carrier allows the detection methods to be carried out in relatively small volumes—thus facilitating scale up and minimising the sample volume required.

The kits will typically incorporate suitable instructions. These instructions permit the methods of the invention to be carried out reliably using the kits of the invention.

BRIEF DESCRIPTION OF THE DRAWING

FIG. 1 shows real time assay results for the PCR assay. The curves shown are, from left to right: 24000 cells, 2400 cells, 240 cells, 0 cells, remaining traces are buffer controls.

EXPERIMENTAL SECTION

The invention will be understood with respect to the following non-limiting examples:

Example 1

Blood Broth Assay for Yeast

Preparation of Assay Solutions:

| | |
|---|---|
| 10x T4 DNA ligase reaction buffer (NEB cat. # B0202S) | |
| 10% Triton-X-100 | (Sigma cat. # T8532) |
| 5% BSA | (Sigma cat. # A7906) |
| 1M Tris Cl pH 7.5 | (from Tris HCl and Tris base, Sigma cat. # T3253, T1503) pH to 7.5 |
| H2O | (Sigma cat. # W4502) through 0.2 μm filter then autoclaved, use this H2O where required in assay |
| 25 DNA | (sequences from MWG) |
| 1M NaOH | (Sigma cat. # 221465) |
| DTT | |

Ceramic lysis beads (1 mm diameter) supplied by Idexx Laboratories Inc. were blocked with 1 ml 5% BSA overnight and washed with 1× reaction buffer, 1 ml of B0202S Resuspend in 1× reaction buffer, 1 ml of B0202S.

DNA components were dissolved (oligonucleotides supplied by MWG Eurofins) at a working concentration of 1 ng/μl in H2O via serial dilutions in 10 mM EDTA (sigma cat. # E7889).

The sequences were:

```
                                         (SEQ ID NO: 1)
S1 ACCAAAATCCCACCACAACAGAACTCACCAACCAAACACACACACAA
CAAC (SEQ ID NO: 2)
S2 CCACGCTCACCTCGGCTCCCTCTTCTCTGACTCCTTCC (SEQ ID NO: 3)
AS GAGGTGAGCGTGGGTTGTTGTGTGTGTGTTTCC (SEQ ID NO: 4)
F  CCCACCACAACAGAACTCACCAACC (SEQ ID NO: 5)
R  GGAAGGAGTCAGAGAAGAGGGAGCC
``` where F and R refer to forward and reverse primers, S1, S2 and AS are the 3 components of the substrate.

Assay Protocol

1. Add 10 ml blood broth (diluted 1:4) to sterile 15 ml falcon tubes
2. Add 10 blocked and washed ceramic beads
3. Add 0.2 ml 10% Triton, invert to mix
4. Spin 4000 rpm for 20 min in bench centrifuge
5. Aspirate supernatant
6. Add 1 ml H2O
7. Resuspend pellet
8. Add 9 ml H2O
9. Add 0.5 ml 5% BSA
10. Add 50 μl 1M NaOH (giving 5 mM NaOH pH12), invert to mix
11. Spin 4000 rpm for 20 min
12. Aspirate supernatant, leaving dry beads, neutralise with 10 ml 50 mM TrisCl pH 7.5, mix by vortex for 20 sec
13. Spin 4000 rpm for 20 min, aspirate supernatant
14. Remove remaining solution
15. Resuspend beads and pelleted yeast cells in 100 μl mechanical lysis mix:
5% BSA 20 μl
1% Triton-X-100 10 μl
1% Tween 20 10 μl
10× T4 DNA ligase reaction buffer 10 μl
AS1318 DNA1 ng/μl 10 μl
1M DTT 1 μl
H2O 39 μl
16. Transfer to mechanical lysis tubes (Sarstedt 2 ml sterile tubes cat. #72. 694. 006)
17. Ribolyse power 5 m/sec for 45 sec, wait 2 mins, then repeat
18. Short centrifuge step (2 min)
19. Incubate 37 deg C for 30 min
20. 2 μl to PCR Thermal Cycle Programme
50 deg 2 min
95 deg 15 min 1×
94 deg 10 sec
72 deg 5 sec 30×

The PCR mix contained 10 μl SYBR Green 2× (Eurogentec mix cat.# RT-SN2X-03+NR), F primer 10 μM 2.25 μl, R primer 10 μM 2.25 μl, H2O 3.5 μl Results The FIGURE shows real time assay results for the PCR assay, 10 curves are (left to right): 24000 cells, 2400 cells, 240 cells, 0 cells, remaining traces are buffer controls.

Example 2

Demonstration of the Inactivation of Host ATP-Dependent Ligase with NaOH

Rationale. This experiment was performed in order to demonstrate the ability of alkali pH to inactivate host ATP-dependent ligase released from mammalian white blood cells.

Method

For Mammalian Cells 10 ml of blood was diluted to 50 ml with water to lyse the red cells.

White cells were collected by centrifugation.

The cells were resuspended in 50 mM hepes pH 7 and lysed by ribolysis as described in step 15 of example 1 above then diluted 100-fold in water.

One aliquot of the lysed cells was treated with 5 mM NaOH pH 12 for 20 min whereas another aliquot remained untreated. After treatment with NaOH the lysed cells were diluted into ligase mix and tested for ligase activity as described above in example 1.

For Bacteria

Cultured *E. coli* was diluted in water and either treated with 5 mM NaOH, 5 mM NaOH and 50% (v/v) BPer (Fisher Cat. No. 78243) (to lyse the bacterial cells) or with Bper only.

After treatment for 20 min, the cells were diluted into ligase mix and tested for ligase activity as described in example 1 except that *E. coli* DNA ligase buffer containing NAD was used.

Results

After PCR, the cycles at which the PCR became positive were recorded (see below).
White cells+NaOH 28.3
White cells−NaOH 19.5
*E. coli*+NaOH 20.5
*E. coli*+NaOH+BPer 15.2
*E. coli*+BPer 15.2

Conclusion

The treatment of the white cells with NaOH reduced the signal generated by PCR by 9 cycles compared to untreated white cells. This is due to inactivation of the host ligase by NaOH. In contrast, *E. coli* lysed with BPer yielded the same PCR signal whether the ligase was treated with NaOH or not. This demonstrates that the ligase present in the bacteria is much more resistant to NaOH alkali treatment. If the bacteria are treated with NaOH only, the signal is low because the bacteria remain intact and the ligase is not released into the assay.

Example 3

Blood Broth Assay for Yeast

The purpose of this experiment is to show that yeast (*Candida albicans* as example) can be detected sensitively even in the presence of blood broth.

Preparation of assays solutions and components of the substrate were as listed above in Example 1.

Assay Protocol

A Typical Assay Protocol is as Follows.
1. To 0.25 ml 10% (v/v) Triton X-100 in a 15 ml centrifuge tube, add 10 ml blood:broth and mix. Note: If spiking with bacteria or fungi, add them at this step.
2. Incubate for 5 min on the bench then centrifuge 3-4000×g for 20 min.
3. Pour off the supernatant and invert tube on a tissue to dry.
4. Add 1 ml H2O and pipette to resuspend.
5. Add 9 ml H2O and invert to mix. Add 1 ml 50 mM NaOH and invert to mix
6. Incubate 5 min on the bench then centrifuge 3-4000×g for 20 min.
7. Pour off supernatant and invert tube to dry.
8. Resuspend pellet in 1 ml 50 mM Tris pH 7.5, transfer to microfuge tube, spin 8,000 rpm 3 min, pipette off supernatant
9. Add 50 µl Ribomix and mix to resuspend pellet.
10. Transfer to a 2 ml ribolysis tube containing ribolysis beads.
11. Ribolyse at power 4 for 20 sec.
12. Place the tube at 37° C. for 30 min for ligation.
13. Spin 8 krpm 3 min
14. Remove 2 µl to PCR.

Ribomix:

| 5% BSA | 10 µl |
|---|---|
| 1% triton | 5 µl |
| 1% tween | 5 µl |
| 10 X rxn buffer | 5 µl (containing ATP/NAD) |
| DNA 0.1 pmol/µl/µl | 5 µl |
| H2O | 20 µl |

PCR mix:

| SYBR Stratagene mix | 10 µl (# 600830) | |
|---|---|---|
| F primer 10 µM | 2 µl | |
| R primer 10 µM | 2 µl | |
| UDGase | 0.4 µl | |
| Sample | 2 µl | |
| Water | 3.6 µl | |
| PCR PROG | 55 deg | 10 min | |
| | 95 deg | 10 min | 1x |
| | 95 deg | 10 sec | |
| | 65 | 10 sec | |
| | 72 | 10 sec | 40x |

DNA sequences (all read 5'-3')

```
                                                 (SEQ ID NO: 6)
AS DNA: UAG UAC UUC GUG GGU UGU UGU CUC UCG CCU

UCC CAG UUC GGC CGU UGU CCG AUA UCG GCU

3' phosphate
                                                 (SEQ ID NO: 7)
S1: GCC GAT ATC GGA CAA CGG CCG AAC TGG GAA GGC GAG AGA CAA CAA C
                                                 (SEQ ID NO: 8)
S2: 5' phosphate CC ACG AAG TAC TAG CTG GCC GTT TGT CAC CGA CGC CTA 3' phosphate
                                                 (SEQ ID NO: 9)
F primer GGA CAA CGG CCG AAC TGG GAA GGC G
                                                 (SEQ ID NO: 10)
R primer TAG GCG TCG GTG ACA AAC GGC CAG C
```

Results

Experiment 1.a

*C. albicans* in culture medium vs *C. albicans* in blood broth (NaOH treated).

When *C. albicans* was measured using the above protocol, with an NaOH treatment step, the results were as shown in Table 1 below:

TABLE 1

| | Culture medium | | | Blood broth | | |
|---|---|---|---|---|---|---|
| Number of *C. albicans* | Ct | Ct difference | Numerical difference from control (fold) | Ct | Ct difference | Numerical difference from control (fold) |
| 390 CFU/mL | 24.1 | 3.5 | 11.3 | 24.5 | 4.6 | 24.3 |
| 98 CFU/mL | 26.1 | 1.5 | 2.8 | 27.0 | 2.1 | 4.3 |
| 25 CFU/mL | 25.3 | 2.3 | 4.9 | 27.7 | 1.4 | 2.6 |
| Control | 27.6 | 0 | | 29.1 | 0 | |

Because each Ct difference represents a two-fold increase in the signal, the figures in the "numerical difference" column are given to show the actual difference. For example, 390 CFU/mL *C albicans* gave an 11.3-fold increase in signal over background or a 3.5 Ct difference in culture medium.

The Results Show:
1. *C. albicans* can be measured sensitively in blood broth.
2. The background signal in blood broth is very low when the NaOH treatment has been used.

Experiment 1b

Effect of High pH Exposure on Blood DNA Ligase Signal

In blood broth that is not treated with NaOH, there is a very high signal even after the blood cells have been removed by the Triton lysis step (step 3 above). This appears to be due to a blood lysis residue containing white cells. An experiment was performed according to the above protocol using 10 mL of sterile human blood diluted to 50 mL in culture medium and measured with and without NaOH treatment, with no fungi present. The pellet at step 6 was diluted 100 fold to keep signals within a reasonable range

TABLE 2

|  | −NaOH | +NaOH |
| --- | --- | --- |
| Blood lysis residue/100 | 19.5 | 26.7 |
| control | 29.5 | 29.5 |

In the absence of NaOH the blood signal even when diluted 100-fold was 10 Ct, far higher than the level seen with small amounts of *C. albicans*. In the presence of NaOH this background signal is reduced to 2.8 Ct. This is a difference of 7.2 Ct or a 150-fold reduction.

Experiment 1c

Effect of High pH Exposure on *C. albicans*

Does high pH lyse *C. albicans* or is the pH effect simply because the organism remains resistant to pH because it remains intact?

*C. albicans* in culture medium were exposed to varying pH for 20 min before being tested for ligase activity as described above but without the lysis step (step 12). This was compared to a routine assay run at pH 7.5 with the lysis step. In this case the high pH was created by exposure to sodium carbonate rather than sodium hydroxide.

TABLE 3

| pH | Ct | Change in Ct | Signal change (fold) |
| --- | --- | --- | --- |
| 7.5 | 29 | 0 | 0 |
| 9.6 | 29.4 | — | — |
| 10.2 | 28.9 | 0.1 | 0 |
| 11.2 | 26.8 | 2.2 | 4.6 |
| 7.5 (lysed) | 26.8 | 2.2 | 4.6 |

The results show that there is no significant signal from *C. albicans* in the absence of a lysis step, until pH 11.2. At this pH the yeast appear to be lysing and giving a signal as strong at that seen in lysed yeast.

If the above experiment is repeated but all the test pH samples are lysed instead, the results are as shown in table 4:

TABLE 4

| pH | Ct | Change in Ct | Signal change (fold) |
| --- | --- | --- | --- |
| 7.5 | 26.2 | 3.6 | 12.1 |
| 9.6 | 27.2 | 2.6 | 6.1 |
| 10.2 | 27.1 | 2.7 | 6.5 |
| 11.2 | 26.5 | 3.3 | 9.8 |
| control | 29.8 | 0 | |

This demonstrates that when the lysed yeast are exposed to high pH they are still able to give a strong signal, with the signal at pH 11.2 almost as high as the signal at pH 7.5. This is in direct contrast to the results using blood.

Experiment 2

Effect of High pH on *Saccharomyces cerevisiae*

The experiment to test the effect of high pH was repeated using lysed and unlysed *Saccharomyces cerevisiae*. The lysis step in the case was to expose the organism to YPER, a yeast lysis agent marketed by Pierce, instead of mechanical lysis.

TABLE 5

|  | Ct | Ct difference | Numerical difference (fold) |
| --- | --- | --- | --- |
| *S. cerevisiae* + YPER | 27.3 | 3.0 | 8 |
| *S. cerevisiae* + NaOH | 28.3 | 2.0 | 4 |
| *S. cerevisiae* + YPER + NaOH | 28.3 | 2.0 | 4 |
| Control | 30.3 | 0 | |

The experiment demonstrates that *S. cerevisiae* shows a good signal after exposure to high pH even though it has been lysed.

Experiment 3

Effect of High pH on *E. coli*

The experiment to test the effect of high pH was repeated using lysed and unlysed *E. coli*. The lysis step in the case was to expose the organism to BPER, a bacterial lysis agent marketed by Pierce, instead of mechanical lysis.

TABLE 6

|  | Ct | Ct difference | Numerical difference (fold) |
| --- | --- | --- | --- |
| *E. coli* + BPER | 24.7 | 5.1 | 34 |
| *E. coli* + NaOH | 26.6 | 3.2 | 9.2 |
| *E. coli* + BPER + NaOH | 23.6 | 6.2 | 74 |
| Control | 29.8 | 0 | |

The experiment demonstrates that *E. coli* shows an excellent signal after exposure to high pH even though it has been lysed.

Experiment 4

Effect of High pH on Purified Bacterial DNA Ligase and Mammalian Ligase

Recombinant *E. coli* DNA ligase (NEB catalogue number M0205) was exposed to pH 10.2 for 20 min and the signal compared to the unexposed enzyme. This was compared to exposure of blood ATP ligase activity after the same period of exposure to pH 10.2.

TABLE 7

|  | Ct | Ct difference | Numerical difference (fold) |
| --- | --- | --- | --- |
| Bacterial DNA ligase − NaOH | 12.0 | 16 | 63,000 |
| *E. coli* + NaOH Control | 11.5 | 16.5 | 93,000 |
| Blood ATP ligase − NaOH | 23.8 | 8.3 | 315 |
| Blood ATP ligase + NaOH | 33.4 | — | 0 |
| Control | 32.1 | | |

The experiment shows the bacterial isolated enzyme (in the presence of NAD, its substrate) to be extremely robust toward exposure to high pH. By contrast the mammalian ligase activity in the presence of ATP was eliminated at the same pH.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

Various publications are cited herein, the disclosures of which are incorporated by reference in their entireties.

The invention claimed is:

1. A method of detecting a ligase expressing microorganism in a sample containing mammalian cells comprising:
   (a) selectively permeabilizing the cell membrane of the mammalian cells in the sample without lysing microorganisms in the sample;
   (b) treating the resultant sample of step (a) under high pH conditions that inhibit the activity of ATP-dependent ligase from mammalian cells but do not inhibit the activity of intracellular microbial ligases;
   (c) lysing microorganisms in the resultant sample of step (b) to release ATP and NAD-dependent ligase;
   (d) contacting the resultant sample of step (c) or a portion of the resultant sample of step (c) with a nucleic acid molecule which is a substrate for microbial ligase in the sample;
   (e) incubating the resultant sample of step (d) under conditions suitable for microbial ligase activity; and
   (f) determining the presence and/or the amount of a ligated nucleic acid molecule resulting from the action of the intracellular microbial ligase present in the resultant sample from step (e) on the microbial substrate nucleic acid molecule to indicate the presence of the ligase-expressing microorganism in the incubated sample resulting from step (e).

2. The method of claim 1, wherein said high pH conditions is at least pH 10.

3. The method of claim 1, wherein the ligase-expressing microorganism comprises fungal or bacterial cells or both.

4. The method of claim 1, wherein the ligase expressed by the microorganism comprises an ATP-dependent ligase, an NAD-dependent ligase or both.

5. The method of claim 4, wherein the presence of NAD-dependent ligase activity in the sample indicates the presence of bacterial cells.

6. The method of claim 1, wherein the high pH conditions that inhibit the activity of ATP-dependent ligase from mammalian cells but which do not inhibit the activity of the microbial ligases comprise treating the sample with sodium hydroxide (NaOH) or sodium carbonate ($Na_2CO_3$).

7. The method of claim 6, wherein:
(a) the NaOH is around 5 mM NaOH;
(b) the pH is around 12;
(c) the treatment is carried out for around 20 minutes; or
(d) a combination thereof.

8. The method of claim 1, wherein lysis of microorganisms in step (c) is performed mechanically.

9. The method of claim 1, wherein the high pH is at least pH 11.

10. The method of claim 1, wherein said method further comprises identifying the microorganism responsible for an infection or a disease associated with the presence of a microorganism.

11. The method claim 1, wherein the same nucleic acid molecule is used as a substrate for both NAD-dependent ligase activity and ATP-dependent ligase activity.

12. A method of detecting fungal or bacterial cells or both in a sample comprising:
(a) selectively permeabilizing the cell membrane of mammalian cells in the sample without lysing microorganisms in the sample;
(b) treating the resultant sample of step (a) under conditions that inhibit the background from mammalian ATP-dependent ligase but do not affect intracellular microbial ATP and NAD-dependent ligases;
(c) lysing microorganisms in the resultant sample of step (b) to release the microbial ATP- and NAD-dependent ligases;
(d) contacting a first portion of the resultant sample of step (c) with a nucleic acid molecule which is a substrate for microbial ATP-dependent ligase in the resultant sample of step (c);
(e) incubating the resultant sample of step (d) under conditions suitable for microbial ATP-dependent ligase activity;
(f) determining the presence, amount, or both of a ligated nucleic acid molecule in the resultant sample of step (e) resulting from the action of the microbial ATP-dependent ligase on the substrate nucleic acid molecule to indicate the presence of fungi and/or bacteria;
(g) contacting the a second portion of the resultant sample of step (c) with a nucleic acid molecule which is a substrate for bacterial NAD-dependent ligase in the sample;
(h) incubating the resultant sample of step (g) under conditions suitable for bacterial NAD-dependent ligase activity; and
(i) determining the presence, amount, or both of a ligated nucleic acid molecule resulting from the action of the bacterial NAD-dependent ligase on the substrate nucleic acid molecule to indicate the presence of bacteria only.

13. The method of claim 12, wherein said high pH conditions is at least pH 10.

14. A method of detecting the microorganism responsible for an infection, or a disease associated with the presence of a bacterial or fungal cell in a sample obtained from a mammalian subject comprising:
(a) selectively permeabilizing the cell membrane of mammalian cells in the sample without lysing microorganisms in the sample;
(b) treating the resultant sample of step (a) under high pH conditions that inhibit the background from mammalian ATP-dependent ligase but which do not affect intracellular microbial ATP- and NAD-dependent ligases;
(c) lysing microorganisms in the resultant sample of step (b) to release the microbial ATP- and NAD-dependent ligases;
(d) contacting a first portion of the resultant sample of step (c) with a nucleic acid molecule which is a substrate for microbial ATP-dependent ligase activity in the sample;
(e) incubating the contacted resultant sample of step (d) under conditions suitable for microbial ATP-dependent ligase activity;
(f) determining the presence, amount, or both of a ligated nucleic acid molecule in the resultant sample of step (e) resulting from the action of the microbial ATP-dependent ligase on the substrate nucleic acid molecule to indicate the presence of fungi and/or bacteria causing the infection;
(g) contacting a second portion of the resultant sample of step (c) with a nucleic acid molecule which acts as a substrate for bacterial NAD-dependent ligase present in the sample;
(h) incubating the resultant sample of step (g) under conditions suitable for NAD-dependent ligase activity; and
(i) determining the presence, amount, or both of a ligated nucleic acid molecule resulting from the action of the bacterial NAD-dependent ligase on the substrate nucleic acid molecule to indicate the presence of bacteria causing the infection.

15. The method of claim 14, wherein said high pH conditions is at least pH 10.

16. A method of detecting fungal cells in a sample comprising:
(a) selectively permeabilizing the cell membrane of mammalian cells in the sample without lysing the fungi in the sample;
(b) treating the resultant sample of step (a) under high pH conditions that inhibit the background signal from mammalian ATP-dependent ligase but do not affect intracellular fungal ATP dependent ligases;
(c) lysing fungal cells in the resultant sample of step (b) to release the fungal ATP-dependent ligases;
(d) contacting the resultant sample of step (c) or a portion of the resultant sample of step (c) with a nucleic acid molecule which is a substrate for fungal ATP-dependent ligase in the sample
(e) incubating the resultant sample of step (d) under conditions suitable for fungal ATP-dependent ligase activity;
(f) determining the presence, amount, or both of a ligated nucleic acid molecule resulting from the action of the fungal ATP-dependent ligase on the substrate nucleic acid molecule to indicate the presence of fungi.

17. The method of claim 16, wherein said high pH conditions is at least pH 10.

18. A method of determining whether a fungus is responsible for an infection, or a disease associated with the presence of a fungal cell in a sample obtained from a subject comprising:
(a) selectively permeabilizing the cell membrane of mammalian cells in the sample without lysing the fungi in the sample;
(b) treating the resultant sample of step (a) under conditions that inhibit the background from mammalian ATP-dependent ligase but do not affect fungal ATP-dependent ligases;
(c) lysing any fungal cells in the resultant sample of step (b) to release the fungal ATP-dependent ligase;

(d) contacting the resultant sample of step (c) with a nucleic acid molecule which is a substrate for fungal ATP-dependent ligase in the resultant sample from step (c);

(e) incubating the resultant sample of step (d) under conditions suitable for fungal ATP-dependent ligase activity; and (f) determining the presence, amount, or both of a ligated nucleic acid molecule resulting from the action of the fungal ATP-dependent ligase on the substrate nucleic acid molecule in the resultant sample from step (e) to indicate the presence of fungi causing the infection or disease.

19. The method of claim 18, wherein said high pH conditions is at least pH 10.

* * * * *

```
                          SEQUENCE LISTING

<160> NUMBER OF SEQ ID NOS: 10

<210> SEQ ID NO 1
<211> LENGTH: 51
<212> TYPE: DNA
<213> ORGANISM: Artificial sequence
<220> FEATURE:
<223> OTHER INFORMATION: Substrate

<400> SEQUENCE: 1
accaaaatcc caccacaaca gaactcacca accaaacaca cacacaacaa c               51

<210> SEQ ID NO 2
<211> LENGTH: 38
<212> TYPE: DNA
<213> ORGANISM: Artificial sequence
<220> FEATURE:
<223> OTHER INFORMATION: Substrate

<400> SEQUENCE: 2
ccacgctcac ctcggctccc tcttctctga ctccttcc                              38

<210> SEQ ID NO 3
<211> LENGTH: 33
<212> TYPE: DNA
<213> ORGANISM: Artificial sequence
<220> FEATURE:
<223> OTHER INFORMATION: Substrate

<400> SEQUENCE: 3
gaggtgagcg tgggttgttg tgtgtgtgtt tcc                                   33

<210> SEQ ID NO 4
<211> LENGTH: 25
<212> TYPE: DNA
<213> ORGANISM: Artificial sequence
<220> FEATURE:
<223> OTHER INFORMATION: Primer

<400> SEQUENCE: 4
cccaccacaa cagaactcac caacc                                            25

<210> SEQ ID NO 5
<211> LENGTH: 25
<212> TYPE: DNA
<213> ORGANISM: Artificial sequence
<220> FEATURE:
<223> OTHER INFORMATION: Primer

<400> SEQUENCE: 5
ggaaggagtc agagaagagg gagcc                                            25

<210> SEQ ID NO 6
<211> LENGTH: 60
<212> TYPE: RNA
<213> ORGANISM: Artificial sequence
<220> FEATURE:
<223> OTHER INFORMATION: Substrate
```

```
<400> SEQUENCE: 6
uaguacuucg uggguuguug ucucucgccu ucccaguucg gccguugucc gauaucggcu    60

<210> SEQ ID NO 7
<211> LENGTH: 46
<212> TYPE: DNA
<213> ORGANISM: Artificial sequence
<220> FEATURE:
<223> OTHER INFORMATION: Substrate

<400> SEQUENCE: 7
gccgatatcg gacaacggcc gaactgggaa ggcgagagac aacaac                   46

<210> SEQ ID NO 8
<211> LENGTH: 38
<212> TYPE: DNA
<213> ORGANISM: Artificial sequence
<220> FEATURE:
<223> OTHER INFORMATION: Substrate

<400> SEQUENCE: 8
ccacgaagta ctagctggcc gtttgtcacc gacgccta                            38

<210> SEQ ID NO 9
<211> LENGTH: 25
<212> TYPE: DNA
<213> ORGANISM: Artificial sequence
<220> FEATURE:
<223> OTHER INFORMATION: Primer

<400> SEQUENCE: 9
ggacaacggc cgaactggga aggcg                                          25

<210> SEQ ID NO 10
<211> LENGTH: 25
<212> TYPE: DNA
<213> ORGANISM: Artificial sequence
<220> FEATURE:
<223> OTHER INFORMATION: Primer

<400> SEQUENCE: 10
taggcgtcgg tgacaaacgg ccagc                                          25
```